US010222390B2

United States Patent
Glass et al.

(10) Patent No.: US 10,222,390 B2
(45) Date of Patent: Mar. 5, 2019

(54) NEAR-INFRARED FLUORESCENT SENSORS FOR BIOLOGICAL AMINES

(71) Applicant: The Curators of the University of Missouri, Columbia, MO (US)

(72) Inventors: Timothy Glass, Columbia, MO (US); Kenneth Hettie, Columbia, MO (US)

(73) Assignee: THE CURATORS OF THE UNIVERSITY OF MISSOURI, Columbia, MO (US)

( * ) Notice: Subject to any disclaimer, the term of this patent is extended or adjusted under 35 U.S.C. 154(b) by 0 days.

(21) Appl. No.: 15/229,716

(22) Filed: Aug. 5, 2016

(65) Prior Publication Data

US 2017/0082645 A1 Mar. 23, 2017

Related U.S. Application Data

(60) Provisional application No. 62/201,413, filed on Aug. 5, 2015.

(51) Int. Cl.
| | |
|---|---|
| C09K 11/07 | (2006.01) |
| G01N 33/94 | (2006.01) |
| C09B 57/02 | (2006.01) |
| G01N 33/58 | (2006.01) |
| C09K 11/06 | (2006.01) |

(52) U.S. Cl.
CPC ........... *G01N 33/942* (2013.01); *C09B 57/02* (2013.01); *C09K 11/06* (2013.01); *C09K 11/07* (2013.01); *G01N 33/582* (2013.01); *G01N 33/9406* (2013.01); *G01N 33/9413* (2013.01); *C09K 2211/1048* (2013.01); *C09K 2211/1051* (2013.01)

(58) Field of Classification Search
CPC .................................................. G01N 33/942
See application file for complete search history.

(56) References Cited

U.S. PATENT DOCUMENTS

| | | |
|---|---|---|
| 3,501,490 A | 3/1970 | Maeder et al. |
| 3,966,755 A | 6/1976 | Schlapfer |
| 4,764,622 A | 8/1988 | Claussen et al. |
| 7,977,120 B2 | 7/2011 | Glass et al. |
| 2009/0011454 A1 | 1/2009 | Glass et al. |

FOREIGN PATENT DOCUMENTS

| | | | |
|---|---|---|---|
| GB | 1010562 A | 11/1965 | |
| GB | 1200852 A | 8/1970 | |
| IN | 2009MUO1306 | * 12/2009 | ........... G01N 33/942 |
| WO | 2014/153533 A1 | 9/2014 | |

OTHER PUBLICATIONS

Jagtap et al., Dyes and Pigments, vol. 91, Issue 1, Oct. 2011, pp. 20-25.*
Jagtap et al., Dyes and Pigments, vol. 82, Issue 1, Jul. 2009, pp. 84-89.*
STN Database, RN 152382-93-9, American Chemical Society, Jan. 20, 1994, 1 page.
Kitamura et al., "Synthesis, Absorption, and Fluorescence Properties and Crystal Structures of 7-Aminocoumarin Derivatives", Journal of Photochemisty and Photobiology A: Chemistry, 2007, pp. 378-386, vol. 188 No. 2.
Li et al., "Coumarin-Derived Fluorescent Chemosensors", Advances in Chemical Sensors, 2012, pp. 121-150, Ch. 6.

* cited by examiner

*Primary Examiner* — Paul V Ward
(74) *Attorney, Agent, or Firm* — Thompson Coburn LLP; Steven M. Ritchey (57) ABSTRACT

A fluorescence sensing compound for separately detecting and visualizing one or more monoamine neurotransmitters in cells, the fluorescence sensing compound having the following formula:

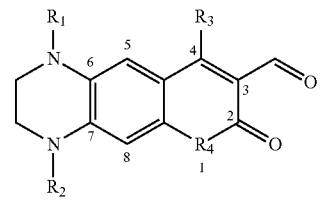

wherein $R_1$ and $R_2$ are each independently selected from the group consisting of hydrogen, alkyl, alkylene, aryl, cycloalkyl;
wherein $R_3$ is selected from the group consisting of hydrogen, alkyl, alkylene, aryl, cycloalkyl, cyano, azido; and
wherein $R_4$ is selected from the group consisting of $(CH_3)_2Si$, O, N, S, and $CH_2$.

9 Claims, 4 Drawing Sheets

NEAR-INFRARED FLUORESCENT SENSORS FOR BIOLOGICAL AMINES

CROSS-REFERENCE TO RELATED APPLICATIONS

This application claims the benefit of provisional application, U.S. Ser. No. 62/201,413, filed Aug. 5, 2015, which is incorporated herein by reference in its entirety.

STATEMENT REGARDING FEDERALLY SPONSORED RESEARCH OR DEVELOPMENT

This invention was made with Government support under Grant No. 5R01 GM059245 awarded by the National Institutes of Health and Grant No. CHE-1112194 awarded by the National Science Foundation. The Government has certain rights in the invention.

FIELD OF THE INVENTION

The present invention relates to fluorescent sensors for intracellular analyte detection. More particularly, the present invention relates to near-infrared fluorescent sensors for detecting and imaging biological amines.

BACKGROUND OF THE INVENTION

Serotonin (5-hydroxytryptamine, 5-HT) is a critical monoamine neurotransmitter in the central nervous system that plays a key role in regulating emotion, mood, and sense of wellbeing. Serotonergic neurons synthesize, store, transport, and release serotonin analogous to other specialized neurons that govern only a single, unique type of monoamine neurotransmitter. The biosynthesis of serotonin transpires within the cell bodies of serotonergic neurons, which are localized to discrete cell clusters within the brainstem. The vesicular monoamine transporter (VMAT) protein stores serotonin within secretory vesicles at high concentrations (50-270 mM) and low pH (~5). Secretory vesicles transport serotonin to axon terminals that innervate most brain regions, thereby maintaining the vesicle pool size and its stores at steady-state levels for continued release of vesicular serotonin into the synaptic cleft.

Deficient serotonin levels are implicated in the etiology of an array of debilitating neuropsychiatric disorders which include anxiety, bipolar disorder, and clinical depression. Selective serotonin reuptake inhibitors (SSRIs) are the most prescribed class of psychotropic medications and utilized as first-line agents to elevate serotonin levels. The persistent administration of SSRIs to serotonergic neurons indirectly dampens negative feedback sensitivity to serotonin release, thereby upregulating the synthesis and transport of serotonin. Accordingly, the enhanced activities promote higher vesicle stores and mobilize a larger vesicle pool size in order to accommodate the progressive release of vesicular serotonin.

Conventional molecular imaging tools for monitoring vesicular serotonin levels or the efficacy of SSRIs to modulate the vesicle pool size and its stores primarily include serotonin autofluorescence, fluorescent probes, and radiolabeled ligands. Unfortunately, the conventional technologies present certain drawbacks such as displaying limited selectivity, allowing for only indirect observation of serotonin, or requiring the use of invasive biomedical devices.

Recent developments in fluorescent molecular sensors have allowed for the selective labeling and direct visualization of similar monoamine neurotransmitters in neuroimaging applications. For such applications, fluorescent molecular sensors that can absorb and emit light within the near-infrared (NIR) optical imaging window (600-900 nm) are highly desirable because NIR light affords limited background fluorescence and high penetration depths in biological samples upon irradiation.

A water-soluble fluorescence-based molecular sensor would permit a unified approach in the selective recognition and visualization of serotonin in vivo and in vitro analyses that limits interference with native neuronal functions. Moreover, a fluorescence-based turn-on molecular sensor possessing spectroscopic properties capable of fluorescence emission in the near infrared (NIR) spectral region (i.e., a wavelength emission greater than 600 nm) would be particularly advantageous by minimizing background from biological analytes (e.g., riboflavin), reducing photodamage to biological samples, and allowing for greater tissue penetration.

Figure 1:
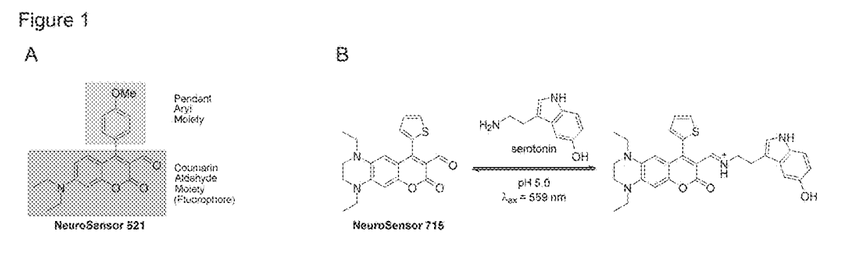
FIG. 1 (A) depicts the structure of NeuroSensor 521 and (B) depicts the binding of NeuroSensor 715 to serotonin.

Although fluorescence-based technologies remain a compelling approach to selectively detect and image serotonin, they have not been a practical approach toward in vivo and ex vivo analyses because they either resulted in biosensors that could not be used in biological models or did not provide a fluorescence turn-on response due to the photophysical tendency of the electron-rich indoleamine moiety to quench the fluorescence response of the fluorophore through photoinduced electron transfer (PET). For example, the NeuroSensor 521 (NS521)-based platform (a coumarin-3-aldehyde scaffold having the following structure) was developed to provide a variety of fluorescence-based turn-on molecular sensors for selective recognition of the catecholamine-based neurotransmitters, norepinephrine and dopamine, and integrated into a tailored approach to comprise a method for the selective labeling and imaging of norepinephrine in secretory vesicles of live and fixed cells that allows for discrimination between secretory cell populations (phenotypes) and continuous observation of neurotransmitter trafficking. See PCT/US2014/031490 filed Mar. 21, 2014, which is incorporated by reference in its entirety. For reference, the structure of NS521 is shown in FIG. 1 (A). In particular, it was discovered that the selection of an appropriate pendant aryl substituent (e.g., p-methoxyphenyl) allows NS521-based compounds to display a marked turn-on fluorescence response separately toward both catecholamines, which typically quench fluorescence emission. Unfortunately, serotonin strongly quenched the fluorescence response of all the compounds based on the NS521 platform.

Therefore, a need exists for a molecular sensor that demonstrates a turn-on NIR fluorescence response upon selective detection of biological amines, such as serotonin.

SUMMARY OF THE INVENTION

In one embodiment, the present invention is directed to a fluorescence sensing compound for separately detecting and visualizing one or more monoamine neurotransmitters in cells, the fluorescence sensing compound having the following formula:

wherein $R_1$ and $R_2$ are each independently selected from the group consisting of hydrogen, alkyl, alkylene, aryl, cycloalkyl;

wherein R₃ is selected from the group consisting of hydrogen, alkyl, alkylene, aryl, cycloalkyl, cyano, azido; and wherein R₄ is selected from the group consisting of (CH₃)₂Si, O, N, S, and CH₂.

In another embodiment, the present invention is directed to a method of detecting monoamine neurotransmitters, the method comprising:
  (a) contacting a biological sample with said fluorescence sensing compound; and
  (b) detecting the presence or absence of fluorescence, wherein the presence of fluorescence indicates the presence of the monoamine neurotransmitters.

BRIEF DESCRIPTION OF THE DRAWINGS

FIGS. 5 (A), (B) and (C) show epinephrine-enriched cells incubated with NS715 (10 μM): (A) $\lambda_{ex}$=458 nm; (B) $\lambda_{ex}$=633 nm; and (C) brightfield image. FIGS. 5 (D), (E), and (F) show norepinephrine-enriched cells incubated with (10 μM): (D) $\lambda_{ex}$=458 nm; (E) $\lambda_{ex}$=633 nm; and (F) brightfield image. Fluorescence was visualized using a 650-710 nm bandpass filter. FIG. 5 (G) shows the average fluorescence intensity for norepinephrine-enriched (NE) and epinephrine-enriched (EP) cells, with NE being 12.42±1.75 and EP being 0.85±0.29 (n=20).

DETAILED DESCRIPTION OF THE INVENTION

In one embodiment, the present invention is directed to fluorescence sensing compound(s) for separately detecting and visualizing one or more monoamine neurotransmitters in cells that exhibit a turn-on NIR fluorescence response toward monoamine-neurotransmitters, such as serotonin. Said fluorescence sensing compound(s) are based upon a coumarin-3-aldehyde scaffold that is derived from a 1,2,3,4-tetrahydroquinoxaline (THQ) framework. In one embodiment, the fluorescence sensing compound has the following structure or formula:

wherein R₁ and R₂ are each independently selected from the group consisting of hydrogen, alkyl, alkylene, aryl, cycloalkyl;

wherein R₃ is selected from the group consisting of hydrogen, alkyl, alkylene, aryl, cycloalkyl, cyano, azido; and wherein R₄ is selected from the group consisting of (CH₃)₂Si, O, N, S, and CH₂.

Design

The foregoing structure was developed for use as a NIR fluorescence-based, turn-on molecular sensor for the selective labeling and visualization of serotonin in synaptic vesicles of neuronal cells. Conceptually, the above-fluorescent compound may be considered as having two distinct moieties from the viewpoint of fluorescence:

(i) a modified bicyclic aromatic aldehyde scaffold (also referred to as the fluorophore), wherein the aldehyde recognition element at the 3-position of the scaffold associates with the analyte amine via iminium ion formation, and wherein the rigid alkylated di-nitrogen species situated at the 6- and 7-positions of the scaffold (C6- and C7-positions) modulate the fluorescence properties of the fluorophore such that the fluorescence response is enhanced upon interaction with serotonin; and (ii) the pendant R₃ group at the 4-position of the scaffold (C4-position) serves to modulate the spectroscopic and photophysical properties (i.e., absorption, emission, and quantum yield profiles) of the fluorophore.

In one embodiment, R₄ of the scaffold is an oxygen (such that the scaffold may be referred to as a modified coumarin aldehyde scaffold) and R₃ is a thiophene moiety as shown if FIG. 1 (B), which is referred as NeuroSensor 715 or NS715. The modified coumarin aldehyde scaffold of NS715 derives from the electron-rich 1,2,3,4-tetrahydroquinoxaline (THQ) framework.

It should be noted that the terms "NeuroSensor 715" and "NS715" may, depending upon the context, be used to refer to the specific structure depicted in FIG. 1 (B) or to structures of the disclosed herein generally. Similarly, the terms "coumarin" and "coumarin scaffold" may, depending upon the context, be used to refer to particular embodiments in which R₄ is N or to the bicyclic aromatic aldehyde scaffold or fluorophore moiety generally.

Figure 2:
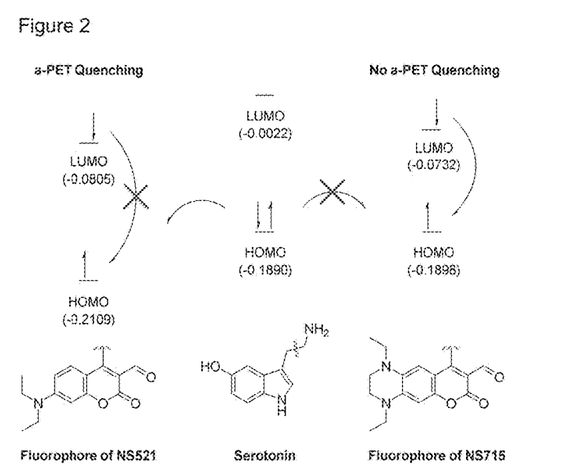
FIG. 2 is a frontier orbital energy diagram and schematic representation of acceptor-excited PET mechanism, wherein the left column identified as "a-PET Quenching" is a schematic representation of the $E_{HOMO}$ value of the corresponding coumarin aldehyde scaffold of derivatives of the NS521 platform and the right column identified as "NO a-PET Quenching" is a schematic representation of the $E_{HOMO}$ of the corresponding modified coumarin aldehyde scaffold of NS715, both in relation to the middle column that is a schematic representation of the $E_{HOMO}$ value of the corresponding 5-hydroxyindole moiety of serotonin.

The aforementioned rigid, electron-donating di-nitrogen species at the C6- and C7-positions of the core structure reinforces orbital alignment by restricting free rotation of the nitrogen atoms and impart pronounced spectroscopic and photophysical properties by simultaneously raising the calculated $E_{HOMO}$ value and lowering the $E_{LUMO}$ value beyond that of 5-hydroxyindoleamine moiety of serotonin to allow for both a substantial enhancement in fluorescence, a red-shifted absorption profile, and a remarkable Stokes' shift of approximately 186 nm. For example, NS715 (which has ethyl groups for $R_1$ and $R_2$, oxygen for $R_4$ at the 1-position, a thiophene moiety for $R_3$ at the C4-position) resulted in a 8.0-fold fluorescence enhancement measured at 780 nm in the NIR spectral region with a binding affinity of 409 $M^{-1}$ in in vitro analyses with serotonin compared to (a) no modulation in the absorption or fluorescence spectrum of NS715 upon interaction with epinephrine due to no binding, and (b) fluorescence quenching (i.e., turn-off fluorescence) upon interaction with NS521 in in vitro analyses. Referring to FIG. 2, left column, serotonin quenched the response of all the NS521 derivatives because the particular underlying fluorophore maintained insufficient energetics (i.e., low $E_{HOMO}$ and $E_{LUMO}$ values), whereas N5715, right column, has sufficient energetics for preventing serotonin from quenching fluorescence emission. Thus, the foregoing structure represents a convenient molecular sensor that allows for integration with a tailored approach to selective labeling and visualization of serotonin in live and fixed neuronal cells.

TERMINOLOGY

Unless otherwise defined, all technical and scientific terms used herein have the same meaning as commonly understood by one of ordinary skill in the art to which this invention belongs. Throughout the specification and claims, a given chemical formula or name shall encompass all optical and stereoisomers as well as racemic mixtures where such isomers and mixtures exist.

As used herein, the term "independently" with respect to references being selected from a group means that each reference may be selected from the entire list set forth as possible selections within the group without regard to the selections of other references having the same or different appellations.

As used herein the term "alkyl" refers to C1-10 inclusive, linear, branched, or cyclic, saturated or unsaturated (i.e., alkenyl and alkynyl) hydrocarbon chains. The alkyl group can be optionally substituted with one or more alkyl group substituents which can be the same or different, where "alkyl group substituent" includes alkyl, amino, halo, arylamino, acyl, hydroxyl, aryloxy, alkoxyl, alkylthio, arylthio, aralkyloxy, aralkylthio, carboxy, alkoxycarbonyl, oxo, cycloalkyl, mesyl, tosyl, and triflic. There can be optionally inserted along the alkyl chain one or more oxygen, sulfur or substituted nitrogen atoms, wherein the nitrogen substituent is hydrogen, lower alkyl (also referred to herein as "alkylaminoalkyl"), or aryl. "Branched" refers to an alkyl group in which a lower alkyl group, such as methyl, ethyl or propyl, is attached to linear alkyl chain.

"Aryl" refers to an aromatic substituent that may be a single ring or multiple rings that are fused together, linked covalently, or linked to a common group such as an ethylene, methylene or oxy moiety. The aromatic rings of the aryl group may each and optionally contain heteroatoms. The aryl group can be optionally substituted with one or more aryl group substituents which can be the same or different, where "aryl group substituent" includes alkyl, aryl, arylalkyl, hydroxy, alkoxyl, aryloxy, arylalkoxyl, carboxy, acyl, halo, nitro, alkoxycarbonyl, aryloxycarbonyl, arylalkoxycarbonyl, acyloxyl, acylamino, aroylamino, carbamoyl, cyano, alkylcarbamoyl, dialkylcarbamoyl, arylthio, alkylthio, alkylene, nitroso, sulfo, and —NRR', where R and R' can be each independently hydrogen, alkyl, aryl, and aralkyl.

As used herein, the terms "substituted alkyl" and "substituted aryl" include alkyl and aryl groups, as defined herein, in which one or more atoms or functional groups of the aryl or alkyl group are replaced with another atom or functional group, including for example, halogen, aryl, alkyl, alkoxyl, hydroxyl, nitro, amino, alkylamino, dialkylamino, sulfate, nitroso, carboxy, and mercapto.

"Cyclic" and "cycloalkyl" refer to a non-aromatic mono- or multicyclic ring system of about 3 to about 10 carbon atoms. The cycloalkyl group can be optionally partially unsaturated. The cycloalkyl group can be also optionally substituted with an alkyl group substituent as defined herein, ox and/or alkylene. There can be optionally inserted along the cyclic alkyl chain one or more oxygen, sulfur or substituted nitrogen atoms, wherein the nitrogen substituent is hydrogen, lower alkyl, or aryl, thus providing a heterocyclic group.

"Alkylene" refers to a straight or branched bivalent aliphatic hydrocarbon group having from 1 to about 10 carbon atoms. The alkylene group can be straight, branched or cyclic. The alkylene group can be also optionally unsaturated and/or substituted with one or more "alkyl group substituents." There can be optionally inserted along the alkylene group one or more oxygen, sulfur or substituted nitrogen atoms, wherein the nitrogen substituent is alkyl as previously described.

Fluorophore $R_4$ at the C1-Position

In at least some of embodiments of the above-described fluorescent compound, $R_4$ at the 1-position is oxygen (i.e., a coumarin-based structure; more particularly, a coumarin-3-aldehyde scaffold) or nitrogen (i.e., a quinolinone-based structure; more particularly, a quinolinone-3-aldehyde scaffold). Results to date have shown that selecting either an oxygen or nitrogen for $R_4$ provides compounds with either a redshifted absorption and fluorescence profile or a molecular handle for appending additional functionalities compared to compounds having a different $R_4$ (e.g., S, or $CH_2$). As such, when R4 at the 1-position is N, the resulting compounds generally tend to be brighter fluorophores.

That said, there may be reasons or end use applications for which one would select something other than oxygen or nitrogen for $R_4$. For example, choosing $R_4$ to be $(CH_3)_2Si$ is expected to dramatically redshift the absorption and fluorescence profiles toward the NIR spectral region, whereas selecting $R_4$ to be sulfur is expected to blue-shift the absorption and fluorescence profiles toward the UV spectral region. Alternatively, selecting a carbon ring member with covalently bonded hydrogens ($CH_2$) is expected to decrease the brightness (i.e., quantum yield and absorbance).

Rigid Alkylated Di-Nitrogen Species at C6- and C7-Positions

The aforementioned rigid alkylated di-nitrogen species at C6- and C7-positions of the scaffold comprise $R_1$ and $R_2$. As set forth above, $R_1$ and $R_2$ are each independently selected from the group consisting of hydrogen, alkyl, alkylene, aryl, cycloalkyl. The selection of $R_1$ and $R_2$ allows for substantial customization or variation of several properties of the fluorescent compound. For example, varying the selection of $R_1$ and $R_2$ allows for modification of selectivity, specificity, solubility, fluorescence, and the attachment of other small molecules, fluorophores, functionalities, biological molecules, or radionuclides/metals. Here, specificity refers to the ability of a molecule to interact with only a specified target, whereas selectivity refers to the ability of a molecule to interact with a specified target only when it is amongst other relevant molecules/systems that would not interfere with the interaction. Thus, specificity and selectivity are not the same.

In an embodiment, $R_1$ and $R_2$ are each the alkyl moiety and are each independently selected from the group moieties consisting of haloalkane, hydroxyalkyl, tosylalkyl, triflatealkyl, alkyl azide, acetyl, trifluoroacetyl, ester, alkyl ester, alkyl sulfonate, and polyethylene glycol. Table A below contains corresponding structures for these moieties and provides a brief description of one or more property(ies) that may be affected, adjusted, modified, or imparted by selecting such a moiety for $R_1$ and/or $R_2$.

TABLE A

| Moiety | Structure | Property(ies) Affected |
|---|---|---|
| haloalkane | (X = F, Cl, Br, I) | pH-sensitivity or the ability to append to other molecules (e.g., proteins in vitro upon using a HaloTag assay) |
| hydroxyalkyl, tosylalkyl, triflatealkyl | (X = OH, OTs, Tf) | pH-sensitivity or the ability to synthetically attach other functional elements |
| alkyl azide | —$N_3$ | Ability to covalently label DNA, RNA, proteins of interest, or pre-label cells via click or inverse electron demand Diels-Alder chemistry |
| acetyl | (acetyl group) | pKa, activation state of fluorophore, and modulation of spectral properties of fluorophore |
| trifluoroacetyl | (—C(O)CF$_3$) | pKa, activation state of fluorophore, and modulation of spectral properties of fluorophore |
| ester | (ester group) | pKa, activation state of fluorophore, and modulation of spectral properties of fluorophore |
| alkyl ester | (—C(O)OH) | Ability to covalently attach other small-molecules or biomolecules that would allow for additional targeting or modified properties |
| alkyl sulfonate | —$SO_3^-$ | enhances solubility in water as well as charged state of molecule |
| polyethylene glycol methyl ether | (PEG) | enhances solubility polar solvents |

Aldehyde Recognition Element

The aldehyde recognition element at the C3-position of the scaffold, as mentioned above, associates with the analyte amine via iminium ion formation. Additionally, aldehyde-derived iminium ion provides hydrogen-bonding capabilities with the carbonyl group of the fluorophore, which assists in modulating the spectroscopic and photophysical profiles of the sensor. The aldehyde-derived iminium ion at the C3-position of the scaffold undergoes further restricted rotation due to the proximity to the C4-position group, which promotes the absorption and emission profiles of the sensor.

Bathochromic-Shift Component: $R_3$ at the C4-Position

As disclosed above, $R_3$ may be selected from the group consisting of hydrogen, alkyl, alkylene, aryl, cycloalkyl, cyano, azido. As with other moieties in the compound, $R_3$ may be selected to affect, adjust, modify, or impart certain properties of, or to, the fluorescent compound.

Alkyl Moiety

In an embodiment, $R_3$ is the alkyl moiety is an unsubstituted, linear alkyl, or an alkynyl moiety. In another embodiment, $R_3$ is a cyano moiety. In another embodiment $R_3$ is an azido moiety. Table B below contains corresponding structures or formulas for these moieties and provides a brief description of the property(ies) that may be affected, adjusted, modified, or imparted by selecting such a moiety for $R_3$.

TABLE B

| Moiety | Structure | Property(ies) Affected |
|---|---|---|
| unsubstituted, linear alkyl | ($C_nH_{2n+1}$) | Ability to incorporate additional recognition elements or atoms/molecules for other labeling purposes |
| alkynyl (or alkyne) | —C≡C— | Absorption and fluorescence profile (redshifts), ability perform click-chemistries, pKa if pH-sensitive |
| cyano | —C≡N | Absorption and fluorescence profile (marked redshifts), pKa if pH-sensitive |
| azido | $N_3$— or —N=N$^+$=N$^-$ | Precursor for forming triazole in cells via click chemistry; imparts relatively long term monitoring of cells (e.g., life of vesicle) by enhancing the reactions of the compound within cells |

Aryl Moiety

In yet another embodiment, $R_3$ is the aryl moiety and is selected from the group of moieties consisting of (i) a benzene-based moiety (monocyclic or polycyclic; and if polycyclic, the rings may be homo- or hetero-cyclic), (ii) a heterocyclopentadiene-based moiety having one or more heteroatoms selected from the group consisting of oxygen and sulfur and nitrogen (monocyclic or polycyclic; and if polycyclic, the rings may be homo- or hetero-cyclic), (iii) tetrazine, (iv) pyridine, and (v) quaternary aminobenzene. Both the benzene-based moiety and heterocyclopentadiene-based moiety may be monocyclic or polycyclic and, if polycyclic, the rings may be homo- or hetero-cyclic. These moieties are discussed in greater detail below. Table C below contains corresponding structures or formulas for these moieties and provides a brief description of the property(ies) that may be affected, adjusted, modified, or imparted by selecting such a moiety for $R_3$.

Benzene-Based Moiety

The benzene-based moiety may be represented by the following structure or formula:

wherein $R_5$, $R_6$, $R_7$, $R_8$, and $R_9$ are each independently selected from the group consisting of hydrogen, alkyl, alkylene, aryl, cycloalkyl, halo, hydroxyl, alkoxyl, aryloxy, alkylthio, arylthio, carboxyl, alkoxycarbonyl, and a constituent of a fused aryl along with the adjacent $R_5$, $R_6$, $R_7$, $R_8$, and $R_9$, as the case may be (e.g., $R_5$ with $R_6$, or $R_6$ with $R_7$, or $R_7$ with $R_8$, or $R_8$ with $R_9$, or $R_5$ with $R_6$ with $R_7$, or $R_5$ with $R_6$ and $R_7$ with $R_8$, or $R_5$ with $R_6$ and $R_8$ with $R_9$, or $R_5$ with $R_6$ with $R_7$ with $R_8$, or $R_5$ with $R_6$ with $R_7$ with $R_8$ with $R_9$, or $R_6$ with $R_7$ with $R_8$, or $R_6$ with $R_7$ and $R_8$ with $R_9$, etc.).

Figure 3:
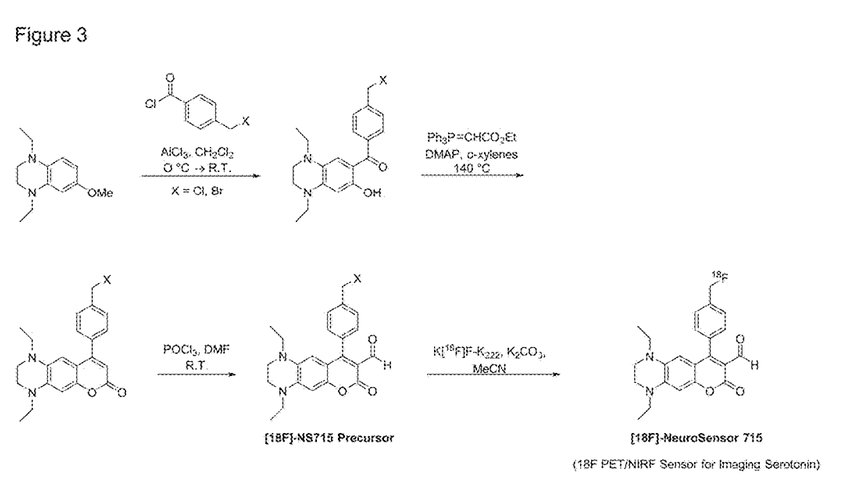
FIG. 3 depicts the process for making an $^{18}F$ radiolabeled derivative of NS715.

One may select a benzene-based moiety for the bathochromic-shift component of the fluorescent compound because these moieties make it relatively easy to append other constituents to the compound to provide different, modified, adjusted, or new or additional functionality(ies) to the fluorescent compound. For example, $^{18}F$ may be added to facilitate use of the compound as a combined PET-Near Infrared Fluorescent Sensor such as that depicted in FIG. 3. Additionally, the selection of a benzene-based moiety may affect the wavelength and brightness of flourescence (e.g., it has been observed that selecting phenyl as $R_3$ instead of thiophene resulted in a wavelength shift of about 5 nm shorter and an increased brightness by about 3 times).

In various embodiments of the present invention, the benzene-based moiety has one of the following structures:

As shown in the foregoing formulas, one such moiety is naphthyl, a naphthalene-based moiety. As described in greater detail below, naphthalene-based moieties may be of particular interest. As such, in one embodiment the benzene-based moiety is a naphthalene-based moiety having the following formula:

wherein $R_5$, $R_6$, $R_7$, $R_8$, $R_9$, $R_{10}$, and $R_{11}$ are each independently selected from the group consisting of hydrogen, alkyl, alkylene, aryl, cycloalkyl, halo, hydroxyl, alkoxyl, aryloxy, alkylthio, arylthio, carboxyl, alkoxycarbonyl, and a constituent of a fused aryl along with the adjacent $R_5$, $R_6$, $R_7$, $R_8$, $R_9$, $R_{10}$, and $R_{11}$, as the case may be (e.g., $R_5$ with $R_6$, or $R_6$ with $R_7$, or $R_7$ with $R_8$, or $R_8$ with $R_9$, or $R_9$ with $R_{10}$, or $R_{10}$ with $R_{11}$, or $R_5$ with $R_6$ with $R_7$, or $R_5$ with $R_6$ and $R_7$ with $R_8$, or $R_5$ with $R_6$ and $R_8$ with $R_9$, or $R_5$ with $R_6$ with $R_7$ with $R_8$, or $R_5$ with $R_6$ with $R_7$ with $R_8$ with $R_9$ with $R_{10}$ with $R_{11}$, or $R_6$ with $R_7$ with $R_8$, or $R_6$ with $R_7$ and $R_8$ with $R_9$, etc.).

Heterocyclopentadiene-Based Moiety

In an embodiment, the bathochromic-shift component, $R_3$, at the C4-position of the scaffold is a heterocyclopentadiene-based moiety. Of particular interest are heterocyclopentadiene-based moieties that are thiophene-based, furan-based, pyrrole-based, and azole-based In one such embodiment the heterocyclopentadiene-based moiety is thiophene-based. In another such embodiment the heterocyclopentadiene-based moiety is furan-based. In another such embodiment, the hetercyclopentadiene-based moiety is pyrrole-based or azole-based.

Thiophene-Based Moiety

In one such embodiment, the heterocyclopentadiene-based moiety is the thiophene-based moiety having the following structure or formula:

wherein $R_5$, $R_6$, and $R_7$ are each independently hydrogen, alkyl, alkylene, aryl, cycloalkyl, halo, hydroxyl, alkoxyl, aryloxy, alkylthio, or arylthio, carboxyl, alkoxycarbonyl, and a constituent of a fused aryl along with the adjacent $R_5$, $R_6$, or $R_7$, as the case may be (i.e., $R_5$ with $R_6$, or $R_6$ with $R_7$, or $R_5$ with $R_6$ with $R_7$).

In another embodiment, the thiophene-based moiety has the following structure or formula:

wherein $R_5$, $R_6$, and $R_7$ are each independently selected from the group consisting of hydrogen, alkyl, alkylene, aryl, cycloalkyl, halo, hydroxyl, alkoxyl, aryloxy, alkylthio, or arylthio, carboxyl, alkoxycarbonyl, and a constituent of a fused aryl along with the adjacent $R_5$, $R_6$, or $R_7$, as the case may be (i.e., $R_5$ with $R_6$).

In various embodiments, the thiophene-based moiety has one of the following structures or formulas:

Furan-Based Moiety

In one embodiment, the aryl moiety is a furan-based moiety, wherein the furan-based moiety has one of the following structures or formulas:

wherein $R_5$, $R_6$, and $R_7$ are each independently selected from the group consisting of hydrogen, alkyl, alkylene, aryl, cycloalkyl, halo, hydroxyl, alkoxyl, aryloxy, alkylthio, or arylthio, carboxyl, alkoxycarbonyl, and a constituent of a fused aryl along with the adjacent $R_5$, $R_6$, or $R_7$, as the case may be (i.e., for the left structure, $R_5$ with $R_6$, or $R_6$ with $R_7$, or $R_5$ with $R_6$ with $R_7$; and for the right structure, $R_5$ with $R_6$).

In one embodiment the furan-based moiety has the following structure or formula:

Pyrrole-Based Moiety

In one embodiment, the aryl moiety is a pyrrole-based moiety, wherein the pyrrole-based moiety has one of the following structures or formulas:

wherein $R_5$, $R_6$, and $R_7$ are each independently selected from the group consisting of hydrogen, alkyl, alkylene, aryl, cycloalkyl, halo, hydroxyl, alkoxyl, aryloxy, alkylthio, or arylthio, carboxyl, alkoxycarbonyl, and a constituent of a fused aryl along with the adjacent $R_5$, $R_6$, or $R_7$, as the case may be (i.e., for the left structure, $R_5$ with $R_6$, or $R_6$ with $R_7$, or $R_5$ with $R_6$ with $R_7$; and for the right structure, $R_5$ with $R_6$).

In one embodiment, the pyrrole-based moiety has the following structure or formula:

Azole-Based Moiety

In one embodiment, the aryl moiety is the azole-based moiety, wherein the azole-based moiety has a has a structure or formula selected from the group consisting of the following:

wherein $R_3$, $R_4$, and $R_5$, are each independently selected from the group consisting of hydrogen, alkyl, alkylene, aryl, cycloalkyl, halo, hydroxyl, alkoxyl, aryloxy, alkylthio, or arylthio, carboxyl, alkoxycarbonyl, and a constituent of a fused aryl if $R_5$ and $R_6$ are adjacent.

In one embodiment, the azole-based moiety is a triazole moiety.

Tetrazine, Pyridine, and Quaternary Aminobenzene

As disclosed above, $R_3$, may be, in different embodiments, be a tetrazine moiety, pyridine moiety, or quaternary aminobenzene. Table C below contains corresponding structures or formulas for these moieties and provides a brief description of the property(ies) that may be affected, adjusted, modified, or imparted by selecting such a moiety for $R_3$.

TABLE C

| Moiety | Structure | Property(ies) Affected |
| --- | --- | --- |
| tetrazine | (tetrazine structure) | Enables attachment of molecules through Cu-free inverse electron demand Diels-Alder reaction |
| pyridine | (2-, 3-, 4-pyridine structures) | pH-sensitivity, modulation of fluorescence via PeT |
| quaternary aminobenzene | $N(Alkyl)_3^+$ (on benzene) | Enables direct attachment of radionuclides ($^{18}F$) or other atoms/molecules via nucleophilic aromatic substitution |

Use of NeuroSensor 715

As indicated above, NeuroSensor 715 is a NIR fluorescence-based, turn-on molecular sensor for the selective recognition and imaging of serotonin in neurosecretory vesicles. NeuroSensor 715 is envisaged to integrate with a tailored approach to comprise a method for the selective labeling and visualization of serotonin in live and fixed cells. The method entails utilizing NeuroSensor 715 to exploit the high concentration of serotonin and acidic environment within secretory vesicles through the formation of a charged complex that prevents translocation across the vesicle membrane and accumulates within secretory vesicles.

NeuroSensor 715 features an aldehyde group that associates with the analyte amine via iminium ion formation and features a pendant thiophene moiety at the 4-position of a modified coumarin aldehyde scaffold derived from the electron-rich THQ framework. The modified coumarin aldehyde scaffold and pendant thiophene moiety are key design parameters that (i) confer a fluorescence turn-on response upon binding to serotonin, and (ii) impart unique spectroscopic properties to NeuroSensor 715 that allow for direct monitoring of the unbound and bound states using a conventional confocal microscope equipped with the standard 458 nm and 559 nm lasers, respectively.

NeuroSensor 715 exhibits an unprecedented 8.0-fold fluorescence enhancement at 715 nm in the NIR spectral region with a binding affinity of 409 $M^{-1}$ in in vitro analyses. NeuroSensor 715 binds to serotonin with a 19-fold higher binding constant compared and to typical primary amines such as glutamate.

EXAMPLES

Example 1: Synthesis of NS715

Figure 4:
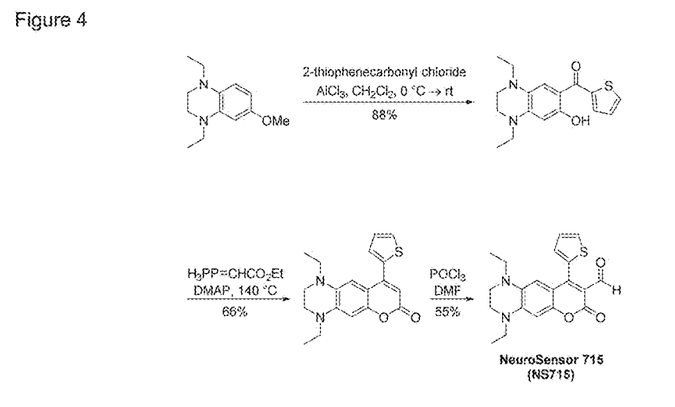
FIG. 4 depicts a synthetic scheme of NS715.

FIG. 4 depicts a synthetic scheme of NS715. As shown in FIG. 4, Compound 1 was acylated and demethylated under Friedel-Crafts conditions to give intermediate 2 in high yield. A high-temperature Wittig reaction with the appropriate phosphorane gave the coumarin core (intermediate 3) in good yield. Regioselective formylation under Vilsmeier conditions completed the synthesis of NS715.

Synthetic Procedures

Compound 1 to Compound 2

Compound 1 (250.0 mg, 1.136 mmol) was dissolved in 11.3 mL $CH_2Cl_2$ and cooled to 0° C. Aluminum chloride (605.2 mg, 4.542 mmol) was added and the solution stirred for 10 min. 2-thiophene carbonyl chloride (166.5 mg, 1.136 mmol) was then added. The mixture stirred for 5 min at 0° C. then warmed to room temperature and stirred for 4 hours while sonicating intermittently. Then 6 M HCl was slowly added to the mixture which stirred another 10 min. The crude product was extracted with $CH_2Cl_2$ (50 mL×3), the organic layers combined and dried over $Na_2SO_4$, and the solvent removed in vacuo. After purifying twice by column chromatography (9:1 $CH_2Cl_2$/EtOAc then 8:2 hexanes/EtOAc), Compound 2 was isolated as a red oil (316.2 mg, 1.000 mmol, 88%): $^1H$ NMR (500 MHz, $CDCl_3$) δ 12.83 (s, 1H), 7.69 (dd, 1H, J=4.0, 1.0 Hz), 7.61 (dd, 1H, J=5.0, 1.0 Hz), 7.14-7.18 (m, 1H), 7.07 (s, 1H), 6.13 (s, 1H), 3.53 (t, 2H, J=5.0 Hz), 3.41 (q, 2H, J=7.0 Hz), 3.24 (q, 2H, J=7.5 Hz), 3.17 (t, 2H, J=5.0 Hz), 1.17-1.25 (m, 6H); $^{13}C$ NMR (125 MHz, $CDCl_3$) δ 186.8, 161.1, 144.5, 143.2, 131.6, 131.1, 127.6, 127.3, 112.1, 108.1, 96.6, 47.8, 45.7, 45.5, 44.9, 10.7, 10.3; IR (neat, $cm^{-1}$) 3101, 2970, 1618, 1524, 1409, 1324, 1217, 1119; HRMS calculated for $C_{17}H_{20}N_2O_2SNa$ (M+Na$^+$): 339.1138. Found: 339.1135.

Compound 2 to Compound 3

Compound 2 (72.5 mg, 0.229 mmol), (carbethoxymethylene)triphenylphosphorane (87.9 mg, 0.252 mmol), DMAP (2.8 mg, 0.023 mmol), and 2 mL o-xylene were combined in a round bottom flask and heated at 140° C. for 4 h. The solvent was boiled off and the remaining crude product was purified via column chromatography (8:2 hexanes/EtOAc) to yield Compound 3 as an orange oil (51.7 mg, 0.176 mmol, 66%): $^1H$ NMR (500 MHz, $CDCl_3$) δ 7.52 (dd, 1H, J=5.0, 1.0 Hz), 7.40 (dd, 1H, J=3.5, 1.0 Hz), 7.18-7.21 (m, 1H), 6.93 (s, 1H), 6.51 (s, 1H), 6.17 (s, 1H), 3.51 (t, 2H, J=5.0 Hz), 3.41 (q, 2H, J=7.5 Hz), 3.24-3.30 (m, 4H), 1.22 (t, 3H, J=7.5 Hz), 1.17 (t, 3H, J=7.0 Hz); $^{13}C$ NMR (125 MHz, $CDCl_3$) δ 162.2, 150.2, 147.9, 140.1, 137.8, 131.9, 128.3, 127.8, 127.7, 108.3, 107.5, 105.6, 97.0, 47.2, 45.7, 45.5, 45.2, 10.3, 10.0; IR (neat, $cm^{-1}$) 2966, 1716, 1699, 1608, 1538, 1418, 1373, 1334; HRMS calculated for $C_{19}H_{20}N_2O_2SNa$ (M+Na$^+$): 363.1138. Found: 363.1133.

Compound 3 to NS715

The Vilsmeier reagent was made by combining 10.8 mL DMF and 5.23 mL $POCl_3$ at 0° C. in a flame-dried round bottom flask. The solution was stirred for 1 h. In a separate dry flask, Compound 3 (66.0 mg, 0.194 mmol) was dissolved in 2 mL DMF and purged with $N_2$. To the starting material was added 0.5 mL of the Vilsmeier reagent and the mixture stirred at ambient temperature for 2.5 h. The mixture was poured over ice chips (100 g), basified to pH 7 with $NaHCO_3$, and extracted with $CH_2Cl_2$ (25 mL×5). The solvent was removed in vacuo without heating and the crude product purified via column chromatography (1:1 hexanes/EtOAc→100% EtOAc→100% acetone) to yield NeuroSensor 715 as a red oil (35.4 mg, 0.096 mmol, 50%): $^1$H NMR (500 MHz, $CDCl_3$) δ 9.90 (s, 1H), 7.60 (dd, 1H, J=5.0, 1.0 Hz), 7.19-7.23 (m, 1H), 7.15 (dd, 1H, J=3.5, 1.0 Hz), 6.45 (s, 1H), 6.33 (s, 1H), 3.57 (t, 2H, J=5.0 Hz), 3.46 (q, 2H, J=7.5 Hz), 3.22 (t, 2H, J=5.0 Hz), 3.13 (q, 2H, J=7.5 Hz), 1.26 (t, 3H, J=7.5 Hz), 1.05 (t, 3H, J=7.5 Hz); $^{13}$C NMR (125 MHz, $CDCl_3$) δ 188.2, 159.6, 153.8, 152.4, 143.8, 133.0, 132.4, 129.6, 128.2, 127.3, 113.1, 109.9, 106.5, 95.8, 47.8, 46.4, 45.4, 44.6, 10.6, 9.6; IR (neat, $cm^{-1}$) 1728, 1695, 1675, 1605, 1503, 1426, 1336; HRMS calculated for $C_{20}H_{20}N_2O_3SNa$ (M+Na$^+$): 391.0868. Found: 391.1078.

Example 2: Validation of the Utility of NS715 Using Chromaffin Cells

Figure 5:
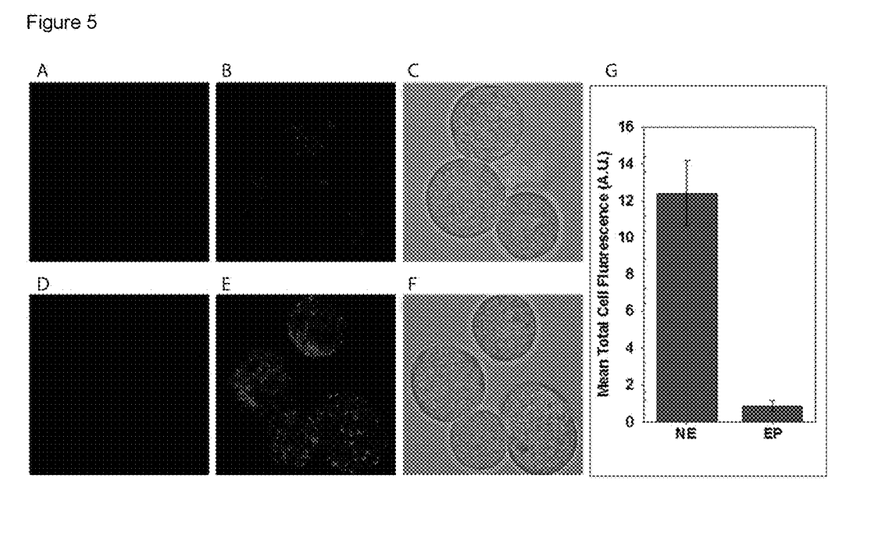

FIG. 5 shows that NS715 may be used to differentiate between cell populations that express distinct neurotransmitter phenotypes. As shown in FIG. 5, populations of chromaffin cells are separated into distinct norepinephrine-enriched and epinephrine-enriched fractions using standard methods. NS715 binds to norepinephrine and strongly fluoresces, but not to epinephrine because it is a secondary-amine neurotransmitter. Both populations of cells were incubated with NS715 (10 µM), washed, and subsequently imaged using confocal microscopy. The unbound UV $\lambda_{max}$=500 nm and the bound UV $\lambda_{max}$=546 nm. The unbound sensor emits at 686 nm and the bound sensor emits at 715 nm. Excitation wavelengths of 458 nm and 633 nm were used to preferentially excite the unbound and bound forms of NS715. Emission for all excitation wavelengths was measured using 650 nm-710 nm bandpass filter.

When excited at 633 nm, only the norepinephrine-enriched cells revealed the punctate pattern with strong fluorescence that is expected for staining high concentrations of norepinephrine in secretory vesicles. The epinephrine-enriched cells showed marginal fluorescence, which can be attributed to NS715 binding to the very low levels of norepinephrine that is present within this type of cell population. Neither cell population showed any appreciable fluorescence upon exciting at 458 nm, thereby indicating that any potentially unbound sensor was removed during the washing step. Further analysis indicated that the average fluorescence intensity of the norepinephrine-enriched cells was 15-fold higher than that of the epinephrine-enriched cells.

Example 2: Spectroscopic Studies

NeuroSensor 715 was screened with various relevant amines via absorption and fluorescence spectroscopy. Steady-state fluorescence spectroscopic studies were performed using a Horiba Scientific Fluorolog-3 Model FL3C-111 spectrofluorometer and data was collected and analyzed using HJY FluorEssence™ 3.5.1.20 software package. UV-visible spectra were recorded on a Varian Cary 1E UV-visible spectrophotometer at 37° C.

Solution Preparations

A 1 mg/mL stock solution of NeuroSensor 715 in DMSO was prepared. A stock solution of NeuroSensor 715 and derivatives in buffer (2×10$^{-5}$ M, 25 mM HEPES, 50 mM $Na_2S_2O_3$, pH 5.0) was prepared. Serotonin, norepinephrine, dopamine, and glutamate stock solutions were prepared by separately dissolving the analytes at the concentration to be used in the titrations with the buffered stock solution of NeuroSensor 715 (thus avoiding dilution of NeuroSensor 715 during the experiment). NeuroSensor 715 was titrated with aliquots of the analyte solution. NeuroSensor 715 derivatives were excited at 559 nm. The slit width was 10 nm for both excitation and emission.

Figure 6:
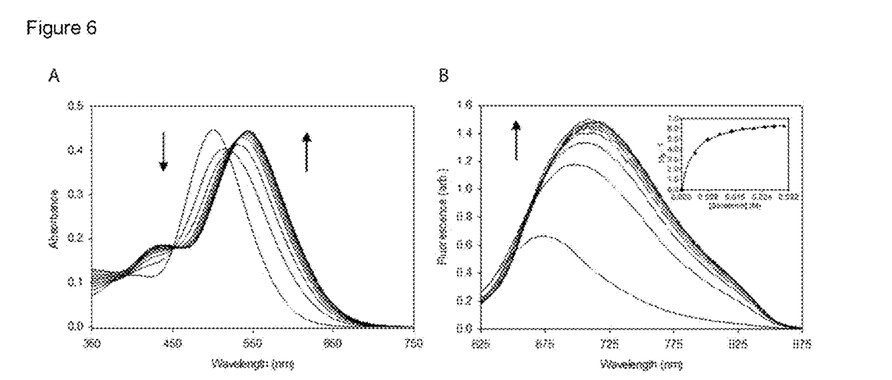
FIG. 6 (A) is an absorbance and (B) is fluorescence spectra of NS715 (20 μM) in buffer (50 mM Na₂S₂O₃, 120 mM NaCl, pH 5.0) adding aliquots of 200 mM serotonin. Inset is the fit to a binding isotherm. $\lambda_{em}$=780 nm.
Figure 7:
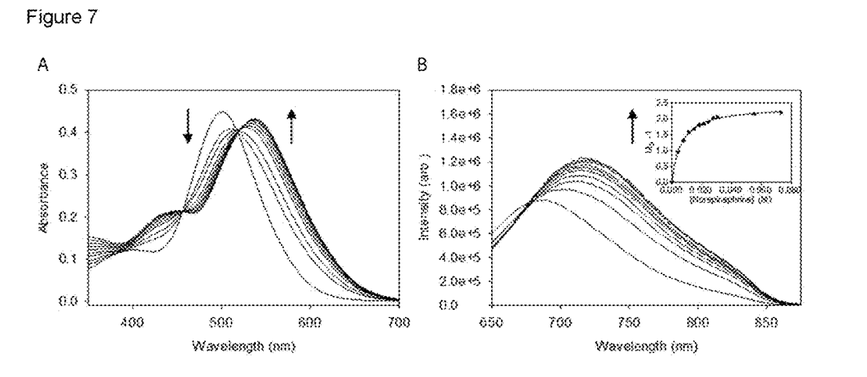
FIG. 7 (A) is an absorbance and (B) is fluorescence spectra of NS715 (20 μM) in buffer (50 mM Na₂S₂O₃, 120 mM NaCl, pH 5.0) adding aliquots of 200 mM norepinephrine. Inset is the fit to a binding isotherm. $\lambda_{em}$=780 nm.
Figure 8:
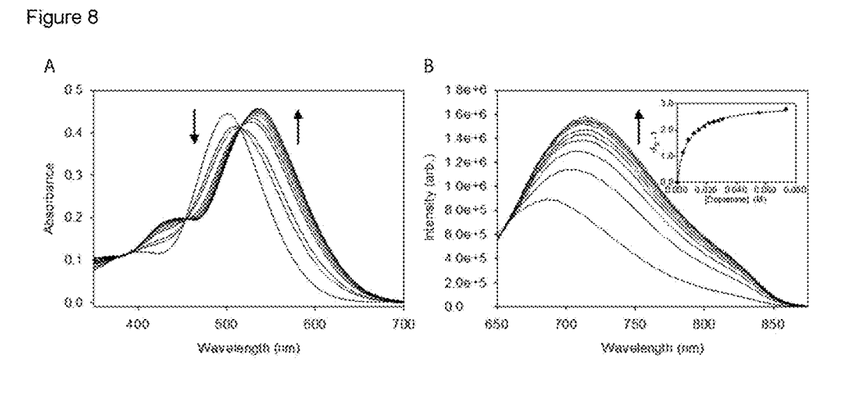
FIG. 8 (A) is an absorbance and (B) is fluorescence spectra of NS715 (20 μM) in buffer (50 mM Na₂S₂O₃, 120 mM NaCl, pH 5.0) adding aliquots of 200 mM dopamine. Inset is the fit to a binding isotherm. $\lambda_{em}$=780 nm.

NeuroSensor 715 binds to all primary amines via iminium ion formation, which produces a red shift in absorption from 500 to 546 nm (FIG. 6 (A)). In fluorescence mode, exciting the unbound NeuroSensor 715 at 559 nm provided fluorescence emission at 686 nm. In fluorescence mode, exciting the bound complex at 559 nm upon adding serotonin produced a marked 8.0-fold fluorescence enhancement at 780 nm (FIG. 6 (B)).

Table D summarizes binding and spectroscopic data for the interaction of NeuroSensor 715 with a number of relevant amines.

TABLE D

Association constants and spectroscopic parameters for the binding of NS715 to various analytes

| amine guest | $K_a$ (M$^{-1}$)$^a$ | $I_{sat}/I_0$$^b$ | $\Delta\lambda_{max, abs}$$^c$ (nm) |
|---|---|---|---|
| serotonin | 409 | 8.0 | 46 |
| dopamine | 145 | 4.0 | 37 |
| norepinephrine | 129 | 3.4 | 37 |
| glutamate | 22.3 | 3.0 | 30 |

$^a$$K_a$ measured by fluorescence spectroscopy, $\lambda_{ex}$ = 559 nm, $\lambda_{em}$ = 780 nm. Error in $K_a$ values are ±10% based on triplicate titrations.
$^b$$I_{sat}$ = fluorescence intensity at saturation taken from the theoretical fit to the binding isotherm.
$^c$Bathochromic shift in absorbance upon saturating with analyte.

Glutamate binds with a low binding affinity of 22.3 M$^{-1}$ that provides a 3.0-fold fluorescence enhancement. The catecholamines norepinephrine and dopamine have on average 6.0-fold higher binding constants compared to glutamate with a binding affinity of 129 M$^{-1}$ and 145 M$^{-1}$ and a 3.0- and 3.4-fold fluorescence enhancement, respectively. Interestingly, the indoleamine serotonin has an 18-fold higher binding constant compared to glutamate with a binding affinity of 409 M$^{-1}$ and 8.0-fold fluorescence enhancement. The bathochromic shift upon analyte binding was 46 nm, 37 nm, and 30 nm for serotonin, the catecholamines, and glutamate, respectively.

NeuroSensor 715 incorporates a pendant thiophene moiety and fused alkylated di-nitrogen species to that derives from the THQ framework to constitute a modified coumarin aldehyde moiety and provides pronounced spectroscopic and photophysical properties. Table E provides a comparison of the spectral characteristics between a benzene-based NeuroSensor 521 derivative, thiophene-based NeuroSensor 521 derivative, and NeuroSensor 715, and highlights the effect of both the incorporation of the thiophene moiety at the C4-position and the electron-rich THQ framework of the coumarin core that situates electron-donating nitrogen substituents at the C6- and C7-positions.

TABLE E

| Sensor | benzene-based NeuroSensor 521 derivative | thiophene-based NeuroSensor 521 derivative | NS715 |
|---|---|---|---|
| $\lambda_{abs}/\lambda_{em}$ (nm)[a] | 452/505 | 462/522 | 500/686 |
| $\lambda_{abs}/\lambda_{em}$ (nm)[b] | 488/520 | 502/539 | 546/715 |
| Stokes shift (nm)[a] | 53 | 60 | 186 |
| Stokes shift (nm)[b] | 32 | 37 | 169 |

[a]Spectroscopic properties of the unbound sensor;
[b]Spectroscopic properties of the sensor saturated with primary amine analyte.

Replacing the pendant benzene moiety with a thiophene moiety on the coumarin aldehyde scaffold of the NeuroSensor 521 platform affords a reasonable bathochromic shift of 10 nm and 17 nm in absorbance and fluorescence emission, respectively, with a maximum absorbance and fluorescence emission at 462 nm and 522 nm, respectively. In doing so, both the unbound and bound Stokes shift increases 53 nm and 32 nm, respectively, for the benzene-based NeuroSensor 521 derivative to the unbound and bound Stokes shift of 60 nm and 37 nm, respectively for the thiophene-based NeuroSensor 521 derivative.

Modify the coumarin aldehyde scaffold by fixing electron-donating nitrogen species at the C6- and C7-positions results in a drastic bathochromic shift in the absorption and emission profiles. The pendant thiophene and THQ-derived modified coumarin aldehyde scaffold afford a noteworthy bathochromic in both the absorption and fluorescence properties with a 500 nm and 546 nm maximum absorbance and a 686 nm and 715 nm maximum fluorescence emission for the unbound and bound complex, respectively. The Stokes shift of both the unbound and bound complex of NeuroSensor 715 increases over 125 nm compared to the thiophene-based NeuroSensor 521 derivative to 186 nm and 169 nm, respectively.

While the invention has been described in connection with specific embodiments thereof, it will be understood that the inventive method is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth and as follows in scope of the appended claims.

What is claimed is:

1. A method of detecting monoamine neurotransmitters, the method comprising:
   (a) contacting a biological sample with a fluorescence sensing compound so that the fluorescence sensing compound binds to one or more monoamine neurotransmitters that are present in in the biological sample; and
   (b) exposing the contacted biological sample to electromagnetic energy of one or more wavelengths capable of inducing fluorescence of bound fluorescence sending compounds and/or unbound fluorescence sensing compound, and detect the presence or absence and/or degree of fluorescence, wherein the presence or absence of fluorescence indicates the presence or absence of one or more monoamine neurotransmitters within the exposed biological sample, respectively, and the degree of fluorescence indicates the degree that one or more monoamine neurotransmitters are present within the exposed biological sample;
   wherein the fluorescence sensing compound has the following formula:

wherein $R_1$ and $R_2$ are each independently selected from the group consisting of hydrogen, alkyl, alkylene, aryl, cycloalkyl;
   wherein $R_3$ is selected from the group consisting of hydrogen, alkyl, alkylene, aryl, cycloalkyl, cyano, azido; and
   wherein $R_4$ is selected from the group consisting of $(CH_3)_2Si$, O, N, S, and $CH_2$.

2. The method of claim 1, wherein:
   $R_1$ and $R_2$ are each the alkyl moiety and are each independently selected from the group moieties consisting of haloalkane, hydroxyalkyl, tosylalkyl, triflatealkyl, alkyl azide, acetyl, trifluoroacetyl, ester, alkyl ester, alkyl sulfonate, and polyethylene glycol; and R$_3$ is one of the following:
(a) the alkyl moiety and is selected from the group of moieties consisting of (i) $C_nH_{2n+1}$ and (ii) alkynyl;
(b) the aryl moiety and is selected from the group of moieties consisting of (i) monocyclic or polycyclic (homo- or hetero-) benzene-based moiety, (ii) monocyclic or polycyclic (homo- or hetero-) heterocyclopentadiene-based moiety having one or more heteroatoms selected from the group consisting of oxygen and sulfur and nitrogen, (iii) tetrazine, (iv) pyridine, and (v) quaternary aminobenzene;
(c) the cyano; or
(d) the azido.

3. The method of claim 2, wherein the heterocyclopentadiene-based moiety is selected from the group consisting of thiophene-based moiety, furan-based moiety, pyrrole-based moiety, and azole-based moiety.

4. The method of claim 3, wherein the aryl moiety is the thiophene-based moiety, wherein the thiophene-based moiety has one of the following formulas:

wherein R$_5$, R$_6$, and R$_7$ are each independently selected from the group consisting of hydrogen, alkyl, alkylene, aryl, cycloalkyl, halo, hydroxyl, alkoxyl, aryloxy, alkylthio, arylthio, carboxyl, alkoxycarbonyl, and a constituent of a fused aryl along with the adjacent R$_5$, R$_6$, or R$_7$, as the case may be.

5. The method of claim 3, wherein the aryl moiety is the furan-based moiety, wherein the furan-based moiety has one of the following formulas:

wherein R$_5$, R$_6$, and R$_7$ are each independently selected from the group consisting of hydrogen, alkyl, alkylene, aryl, cycloalkyl, halo, hydroxyl, alkoxyl, aryloxy, alkylthio, arylthio, carboxyl, alkoxycarbonyl, and a constituent of a fused aryl along with the adjacent R$_5$, R$_6$, or R$_7$, as the case may be.

6. The method of claim 3, wherein the aryl moiety is the pyrrole-based moiety, wherein the pyrrole-based moiety has one of the following formulas:

wherein R$_5$, R$_6$, and R$_7$ are each independently selected from the group consisting of hydrogen, alkyl, alkylene, aryl, cycloalkyl, halo, hydroxyl, alkoxyl, aryloxy, alkylthio, arylthio, carboxyl, alkoxycarbonyl, and a constituent of a fused aryl along with the adjacent R$_5$, R$_6$, or R$_7$, as the case may be.

7. The method of claim 3, wherein the aryl moiety is the azole-based moiety, wherein the azole-based moiety has a has a formula selected from the group consisting of the following:

wherein R$_5$ and R$_6$ are each independently selected from the group consisting of hydrogen, alkyl, alkylene, aryl, cycloalkyl, halo, hydroxyl, alkoxyl, aryloxy, alkylthio, or arylthio, carboxyl, alkoxycarbonyl, and a constituent of a fused aryl if R$_5$ and R$_6$ are adjacent.

8. The method of claim 2, wherein the aryl moiety is the benzene-based moiety, wherein the benzene-based moiety has the following formula:

wherein R$_5$, R$_6$, R$_7$, R$_8$, and R$_9$ are each independently selected from the group consisting of hydrogen, alkyl, alkylene, aryl, cycloalkyl, halo, hydroxyl, alkoxyl, aryloxy, alkylthio, arylthio, carboxyl, alkoxycarbonyl, and a constituent of a fused aryl along with the adjacent R$_5$, R$_6$, R$_7$, R$_8$, and R$_9$, as the case may be.

9. The method of claim 8, wherein the benzene-based moiety is a naphthalene-based moiety having the following formula:

wherein R$_5$, R$_6$, R$_7$, R$_8$, R$_9$, R$_{10}$, and R$_{11}$ are each independently selected from the group consisting of hydrogen, alkyl, alkylene, aryl, cycloalkyl, halo, hydroxyl, alkoxyl, aryloxy, alkylthio, arylthio, carboxyl, alkoxycarbonyl, and a constituent of a fused aryl along with the adjacent $R_5$, $R_6$, $R_7$, $R_8$, $R_9$, $R_{10}$, and $R_{11}$, as the case may be.

* * * * *

UNITED STATES PATENT AND TRADEMARK OFFICE
CERTIFICATE OF CORRECTION

PATENT NO. : 10,222,390 B2
APPLICATION NO. : 15/229716
DATED : March 5, 2019
INVENTOR(S) : Timothy Glass and Kenneth Hettie It is certified that error appears in the above-identified patent and that said Letters Patent is hereby corrected as shown below:

In the Specification

At STATEMENT REGARDING FEDERALLY SPONSORED RESEARCH OR DEVELOPMENT, replace "5R01 GMO59245" with "R01 GMO59245".

Signed and Sealed this
Fifteenth Day of November, 2022

Katherine Kelly Vidal
Director of the United States Patent and Trademark Office